United States Patent
Son et al.

(10) Patent No.: US 11,180,784 B2
(45) Date of Patent: Nov. 23, 2021

(54) **MICROORGANISM OF THE GENUS *CORYNEBACTERIUM* PRODUCING L-AMINO ACIDS AND A METHOD FOR PRODUCING L-AMINO ACIDS USING THE SAME**

(71) Applicant: CJ Cheiljedang Corporation, Seoul (KR)

(72) Inventors: Seung-ju Son, Gyeonggi-do (KR); Byoung Hoon Yoon, Seoul (KR); Kwang Woo Lee, Gyeonggi-do (KR); Seon Hye Kim, Gyeonggi-do (KR); Hyo Jeong Byun, Gyeonggi-do (KR); Jin Sook Chang, Gyeonggi-do (KR); Hyung Joon Kim, Seoul (KR); Yong Uk Shin, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 16/344,205

(22) PCT Filed: Jan. 25, 2019

(86) PCT No.: PCT/KR2019/001067
§ 371 (c)(1),
(2) Date: Apr. 23, 2020

(87) PCT Pub. No.: WO2019/147059
PCT Pub. Date: Aug. 1, 2019

(65) Prior Publication Data
US 2020/0362374 A1    Nov. 19, 2020

(30) Foreign Application Priority Data
Jan. 25, 2018 (KR) .......................... 10-2018-0009633

(51) Int. Cl.
*C12P 13/08* (2006.01)
*C07K 14/34* (2006.01)

(52) U.S. Cl.
CPC .............. *C12P 13/08* (2013.01); *C07K 14/34* (2013.01)

(58) Field of Classification Search
None
See application file for complete search history.

(56) References Cited

U.S. PATENT DOCUMENTS

2015/0329883 A1    11/2015    Chung et al.

FOREIGN PATENT DOCUMENTS

| CN | 1596267 A | 3/2005 |
|----|-----------|--------|
| KR | 10-0159812 B1 | 11/1998 |
| KR | 10-0924065 B1 | 10/2009 |
| KR | 10-1208480 B1 | 12/2012 |
| KR | 20150133091 A | 11/2015 |
| KR | 101793328 | 1/2017 |

OTHER PUBLICATIONS

Kirchner et al. (J. of Biotech., vol. 104, pp. 287-299, 2003).*
NCBI Reference Sequence: WP_003855789.1 (Aug. 29, 2013) MULTISPECIES: WhiB family transcriptional regulator [*Corynebacterium*], (downloaded Sep. 2, 2021 in one page).
Multispecies: WhiB family transcriptional regulator [*Corynebacterium*], NCBI Reference Sequence: WP_003863319.1, Jan. 8, 2020.
Office Action issued in Chinese Patent Application No. 201980000870.X, dated Apr. 17, 2020.
Office Action issued in Taiwanese Patent Application No. 10920270460, dated Mar. 25, 2020.

* cited by examiner

*Primary Examiner* — Hope A Robinson
(74) *Attorney, Agent, or Firm* — Knobbe Martens Olson & Bear LLP

(57) ABSTRACT

A microorganism of the genus *Corynebacterium* producing L-amino acids, and a method of producing L-amino acids using the same.

2 Claims, No Drawings
Specification includes a Sequence Listing.

MICROORGANISM OF THE GENUS *CORYNEBACTERIUM* PRODUCING L-AMINO ACIDS AND A METHOD FOR PRODUCING L-AMINO ACIDS USING THE SAME

CROSS-REFERENCE TO RELATED APPLICATIONS

This application is a U.S. National Phase Application of PCT International Application No. PCT/KR2019/001067, filed on Jan. 25, 2019, designating the United States of America, which is an International Application of and claims the benefit of priority to Korean Patent Application No. 10-2018-0009633, filed on Jan. 25, 2018, the entire contents of which are incorporated herein by reference.

SEQUENCE LISTING STATEMENT

The present application contains a Sequence Listing, which is being submitted via EFS-Web on even date herewith. The Sequence Listing is submitted in a file entitled "Sequence_Listing_HAN030-007APC.txt," which was created on Apr. 23, 2019, and is approximately 4 kb in size. This Sequence Listing is hereby incorporated by reference.

TECHNICAL FIELD

The present disclosure relates to a microorganism of the genus *Corynebacterium* producing L-amino acids, and a method of producing L-amino acids using the same.

BACKGROUND ART

L-amino acids are basic structural units of proteins, and used as important materials for pharmaceuticals, food additives, animal feeds, nutrients, pesticides, bactericides, etc. Among L-amino acids, L-lysine is an essential amino acid that is not biosynthesized in the living body and is known to be necessary for growth promotion, calcium metabolism, promotion of gastric juice secretion, and resistance to diseases. L-lysine is widely used in feeds, medical products, foods, etc. Additionally, L-valine is also one of essential amino acids and is known to have an antioxidant effect and an effect of directly promoting protein synthesis of muscle cells. L-valine is used in health supplements, medical products, foods, feeds, fragrances, hair and skin conditioners, etc.

Meanwhile, a strain of the genus *Corynebacterium*, especially *Corynebacterium glutamicum* is a gram-positive microorganism frequently used in producing L-amino acids and other useful substances. Many studies have been conducted to develop a microorganism with high production efficiency and a fermentation technology for producing the amino acids. For example, target material-specific approaches to increase expression of a gene encoding an enzyme involved in amino acid biosynthesis or to remove unnecessary genes in amino acid biosynthesis in a strain of the genus *Corynebacterium* are mainly used (Korean Patent Nos. 10-0924065 and 1208480). In addition to these methods, a method of deleting genes which are not involved in the amino acid production and a method of deleting genes of which specific functions in the amino acid production are not known are also used. However, there is still a demand for researches on a method capable of efficiently producing L-amino acids with a high yield.

Under this background, the present inventors have conducted intensive studies to develop a microorganism capable of producing L-amino acids with a high yield, and as a result, they found that when a specific gene is inactivated, production yields of L-amino acids are increased, thereby completing the present disclosure.

DISCLOSURE

Technical Problem

An object of the present disclosure is to provide a microorganism of the genus *Corynebacterium* producing L-amino acids, wherein the activity of a protein composed of an amino acid sequence of SEQ ED NO: 1 is inactivated.

Another object of the present disclosure is to provide a method of producing L-amino acids using the microorganism.

Still another object of the present disclosure is to provide a use of the microorganism for enhancing productivity of L-amino acids.

Still another object of the present disclosure is to provide a method of enhancing productivity of L-amino acids, comprising: inactivating the activity of a protein composed of the amino acid sequence of SEQ ID NO: 1 of the present disclosure in a microorganism of the genus *Corynebacterium*.

Technical Solution

The present disclosure will be described in detail as follows. Meanwhile, descriptions and embodiments disclosed herein may also be applied to other descriptions and embodiments. In other words, all combinations of various elements disclosed herein fall within the scope of the present disclosure. Further, the scope of the present disclosure is not limited by specific descriptions described below.

In order to achieve the above objects, an aspect of the present disclosure provides a microorganism of the genus *Corynebacterium* producing L-amino acids, wherein the activity of a protein composed of an amino acid sequence of SEQ ID NO: 1 is inactivated.

As used herein, the term "L-amino acid" may include all L-amino acids which may be produced by a microorganism from many different kinds of carbon sources through metabolic processes. Specifically, the L-amino acid may include basic amino acids such as L-lysine, L-arginine, L-histidine, etc., non-polar amino acids such as L-valine, L-leucine, L-glycine, L, isoleucine, L, alanine, L-proline, L-methionine, etc., polar amino acids such as L-serine, L-threonine, L-cysteine, L-asparagine, L-glutamine, etc., aromatic amino acids such as L-phenylalanine, L-tyrosine, L-tryptophan, etc., acidic amino acids such as L-glutamic acid, L-aspartic acid, aliphatic amino acids such as L-alanine, L-valine, L-isoleucine, L-serine, etc., and branched-chain amino acids such as L-valine, L-leucine, L-isoleucine, etc. In the present disclosure, the L-amino acid may be more specifically basic amino acids, aliphatic amino acids, branched-chain amino acids, and much more specifically, L-lysine or L-valine, but is not limited thereto. The L-amino acid may include any amino acid without limitation, as long as its productivity is increased when the activity of the protein composed of the amino acid sequence of SEQ ID NO: 1 of the present disclosure is inactivated.

As used herein, the term "protein composed of the amino acid sequence of SEQ ID NO: 1" refers to a protein which is, encoded by NCgl0275 gene, intrinsically present in a microorganism of the genus *Corynebacterium*, and specifically, a regulatory protein composed of the amino acid sequence of SEQ ID NO: 1 which is intrinsically present in a microorganism of the genus *Corynebacterium*. The amino acid sequence of SEQ ID NO: 1 and a polynucleotide sequence of a gene encoding the protein may be obtained from a known database, for example, GenBank of NCBI, etc., but are not limited thereto. Further, the protein may be a protein including the amino acid sequence of SEQ ID NO: 1, a protein essentially consisting of the amino acid sequence of SEQ ID NO: 1, or a protein composed of the amino acid sequence of SEQ ID NO: 1, but is not limited thereto.

Further, the protein of the present disclosure may be composed of an amino acid sequence having 80% or more homology with SEQ ID NO: 1 as well as the amino acid sequence of SEQ ID NO: 1. The protein composed of the amino acid sequence having 80% or more homology with the amino acid sequence of SEQ ID NO: 1 may include a protein composed of an amino acid sequence having 80% or more, specifically 83% or more, 84% or more, 88% or more, 90% or more, 93% or more, 95% or more, or 97% or more homology or identity with the amino acid sequence of SEQ ID NO: 1. It is apparent that any amino acid sequence having deletion, modification, substitution, conservative substitution, or addition in part of the sequence is also included as the amino acid sequence having homology or identity with the sequence in the scope of the present disclosure, as long as it is an amino acid sequence having a biological activity substantially identical to or corresponding to that of the amino acid sequence of SEQ ID NO: 1.

In the present disclosure, although described as "a protein or polypeptide composed of a particular SEQ ID NO.", it obviously belongs to the scope of the present disclosure that it may comprise a protein has an amino acid sequence with deletion, modification, substitution, conservative substitution or insertion of a part of the sequence, as long as the protein having an activity the same as or corresponding to that of a polypeptide which consists of an amino acid sequence of the corresponding SEQ ID NO. Even when a polypeptide comprises an amino acid sequence of a particular SEQ ID NO., it obviously belongs to the scope of the present disclosure.

Further, a probe that can be prepared from a known gene sequence, for example, a sequence encoding a protein having the activity of the protein consisting of the amino acid sequence of SEQ ID NO: 1 by hybridizing under stringent conditions with a complementary sequence to all or a part of the polynucleotide sequence, can be included without limitation.

For example, the protein composed of the amino acid sequence of SEQ ID NO: 1 may be encoded by a gene including a polynucleotide sequence of SEQ ID NO: 2. Further, the protein composed of the amino acid sequence of SEQ ID NO: 1 may be encoded by a gene including the polynucleotide sequence of SEQ ID NO: 2, a gene essentially consisting of the polynucleotide sequence of SEQ ID NO: 2, or a gene composed of the polynucleotide sequence of SEQ ID NO: 2, but is not limited thereto.

Further, the polynucleotide sequence of SEQ ID NO: 2 may include a polynucleotide sequence having at least 80% homology with SEQ ID NO: 2 as well as the polynucleotide sequence of SEQ ID NO: 2.

Specifically, any polynucleotide sequence is included in the scope of the present disclosure, as long as it may encode a protein including an amino acid sequence having at least 80% homology with the SEQ ID NO: 1. The protein may be encoded by a gene including a polynucleotide sequence having 80% or more, specifically 83% or more, 84% or more, 88% or more, 90% or more homology, 93% or more, 95% or more, or 97% or more homology or identity with the polynucleotide sequence of SEQ ID NO: 2.

It is also apparent that in the polynucleotide sequence of SEQ ID NO: 2, polynucleotides translated into the protein composed of the amino acid sequence of SEQ ID NO: 1 or a protein having homology therewith due to codon degeneracy is also included. A probe prepared from a known nucleotide sequence, for example, any sequence which hybridizes with a sequence complementary to all or part of the polynucleotide sequence under stringent conditions to encode a protein having the activity of the protein composed of the amino acid sequence of SEQ ID NO: 1 may be also included without limitation. The "stringent conditions" mean conditions under which specific hybridization between polynucleotides is allowed. Such conditions are specifically described in a literature (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York). The stringent conditions may include, for example, conditions under which genes having high homology, 40% or higher homology, specifically 90% or higher homology, more specifically 95% or higher homology, much more specifically 97% or higher homology, still much more specifically 99% or higher homology are hybridized with each other and genes having homology lower than the above homology are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS. Hybridization requires that two polynucleotides contain complementary sequences, although depending on the stringency of the hybridization, mismatches between bases are possible. The term "complementary" is used to describe the relationship between nucleotide bases that are hybridizable to one another. For example, with respect to DNA, adenosine is complementary to thymine and cytosine is complementary to guanine. Therefore, the present disclosure may also include an isolated polynucleotide fragment complementary to the entire sequence as well as a polynucleotide sequence substantially similar thereto.

Specifically, the polynucleotide having homology may be detected using hybridization conditions including a hybridization step at a Tm value of 55° C. under the above-described conditions. Further, the Tm value may be 60° C., 63° C., or 65° C., but is not limited thereto, and appropriately controlled by those skilled in the art depending on the purpose thereof.

As used herein, the term "homology" or "identity" refers to a degree of matching with a given amino acid sequence or polynucleotide sequence, and the homology may be expressed as a percentage. The terms "homology" and "identity" are often used interchangeably with one another. In the present disclosure, a homology sequence having an activity which is identical or similar to the given amino acid sequence or polynucleotide sequence is expressed as "% homology".

The homology or identity to the amino acid or polynucleotide sequence may be determined by, for example, algorithm BLAST [see Karlin and Altschul, Pro. Natl. Acad. Sci. USA, 90, 5873 (1993)] or FASTA by Pearson [see Methods Enzymol., 183, 63(1990)]. Based on this algorithm BLAST, a program called BLASTN or BLASTX has been developed [see www.ncbi.nlm.nih.gov].

Further, homology, similarity, or identity between the amino acid or polynucleotide sequences may be determined by comparing sequences using southern hybridization under stringent conditions. The stringent conditions are within the scope of the corresponding technology and may be determined by a method understood by those skilled in the art (for example, J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

As used herein, the phrase "activity of a protein composed of the amino acid sequence of SEQ ID NO: 1 is inactivated" means that the protein is not expressed at all, or the protein is expressed but exhibits no activity or a reduction in the activity, as compared with that of the native wild-type strain, parent strain, or that of a strain having no modification in the protein composed of the amino acid sequence of SEQ ID NO: 1. In this regard, the reduction refers to a concept including a case where the activity of a protein itself is lower than that of a protein originally possessed in a microorganism due to modification or deletion of a gene encoding the protein, a case where the level of overall protein activity in cells is lower than that of the native strain or that of the strain before modification due to inhibition of expression or translation of the gene encoding the protein, or a combined case thereof.

In the present disclosure, the inactivation may be achieved by various well-known methods in the art. Examples of the methods may include 1) a method of deleting the entirety or part of the gene encoding the protein; 2) a method of modifying an expression control sequence so that expression of the gene encoding the protein is reduced; 3) a method of modifying the sequence of the gene encoding the protein so that the activity of the protein is removed or attenuated; 4) a method of introducing an antisense oligonucleotide (e.g., antisense RNA) which complementarily binds to a transcript of the gene encoding the protein; 5) a method of making the attachment of a ribosome impossible by forming a secondary structure by adding a Shine-Dalgarno sequence and its complementary sequence on the front end of the Shine-Dalgarno sequence of the gene encoding the protein; 6) a method of reverse transcription engineering (RTE), which adds a promoter to be reversely transcribed on the 3' terminus of the open reading frame (ORF) of the polynucleotide sequence of the gene encoding the protein, etc., and may also include a combination thereof, but are not particularly limited thereto.

Specifically, the method of deleting part or the entirety of the gene encoding the protein may be performed by substituting a polynucleotide encoding an endogenous target protein within the chromosome with a polynucleotide or a marker gene where part of the nucleotide sequence is deleted, via a vector for chromosomal insertion into the microorganism. In an exemplary embodiment of the method of deleting part or the entirety of the polynucleotide, a method of deleting the polynucleotide by homologous recombination may be used, but is not limited thereto. In another exemplary embodiment of the method of deleting part or the entirety of the polynucleotide, a mutation may be induced using light such as UV, or chemicals, and a strain having the deleted target gene is selected from the obtained mutants.

The method of deleting the gene may include a method of using a genetic recombination technique. For example, a polynucleotide sequence or a vector including a polynucleotide sequence having homology with a target gene is introduced into a microorganism to cause homologous recombination. Further, the polynucleotide sequence or vector to be introduced may include a dominant selection marker, but is not limited thereto.

Further, the method of modifying the expression control sequence may be achieved by applying a variety of methods well known in the art. For example, the method may be carried by inducing a modification of the expression control sequence in the polynucleotide sequence via deletion, insertion, non-conservative or conservative substitution, or a combination thereof to further attenuate the activity of the expression control sequence, or by substituting the expression control sequence with a polynucleotide sequence having a weaker activity. The expression control sequence may include a promoter, an operator sequence, a sequence encoding a ribosome-binding region, and sequences controlling the termination of transcription and translation, but is not limited thereto.

Furthermore, the method of modifying the nucleotide sequence may be carried out by inducing a modification in the sequence via deletion, insertion, non-conservative or conservative substitution, or a combination thereof in the nucleotide sequence to further attenuate the enzyme activity, or by substituting the nucleotide sequence with a nucleotide sequence which was improved to have weaker activity or a nucleotide sequence which was improved to have no activity, but is not limited thereto.

As used herein, the term "microorganism producing L-amino acids" may refer to a microorganism naturally having an ability to produce L-amino acids or a microorganism which is prepared by imparting an ability to produce L-amino acids to a parent strain having no ability to produce L-amino acids. For example, the microorganism producing L-amino acids may be a microorganism in which the activity of the protein composed of the amino acid sequence of SEQ ID NO: 1 is inactivated. Additionally, the microorganism producing L-amino acids may be a microorganism in which expression of a gene encoding an enzyme involved in the biosynthetic pathway of L-amino acids is enhanced or an enzyme involved in the degradation pathway is inactivated. Alternatively, the microorganism producing L-amino acids may be a microorganism obtained by inactivating the activity of the protein composed of amino acid sequence of SEQ ID NO: 1 in the parent strain in which expression of the gene encoding the enzyme involved in the biosynthetic pathway of L-amino acids is enhanced or the enzyme involved in the degradation pathway is inactivated. The microorganism producing L-amino acids may be prepared by applying various known methods.

In the present disclosure, the "microorganism of the genus *Corynebacterium*" may include all microorganisms of the genus *Corynebacterium*, specifically, *Corynebacterium glutamicum, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris*, or *Corynebacterium flavescens*, and more specifically may be *Corynebacterium glutamicum*.

The microorganism of the genus *Corynebacterium* producing L-amino acids, in which the activity of a protein composed on the amino acid sequence of SEQ ID NO: 1 of the present disclosure is inactivated, may be a microorganism in which the L-amino acid productivity is improved. Specifically, the microorganism may be a microorganism having the improved L-amino acid productivity compared to an unmodified strain. The unmodified strain may be a native wild-type strain, a parent strain, or an unmodified strain in which a protein composed of the amino acid sequence of SEQ ID NO: 1 is not inactivated.

Another aspect of the present disclosure provides a method of producing L-amino acids, the method including the steps of culturing the microorganism according to the present disclosure in a medium; and recovering L-amino acids from the microorganism or the medium.

The microorganism according to the present disclosure is the same as described above.

In the method of the present disclosure, culturing of the microorganism of the genus *Corynebacterium* may be carried out using any culturing conditions and method known in the art.

As used herein, the term "culturing" means that a microorganism is allowed to grow under artificially controlled environmental conditions. In the present disclosure, the method of producing L-amino acids using the microorganism producing L-amino acids may be carried out using a method widely known in the art. Specifically, the culturing may be carried out by a batch process, a fed batch or repeated fed batch process in a continuous manner, but is not limited thereto. Any medium for culturing may be used without limitation, for example, the culture medium for the *Corynebacterium* strains is known in the art (e.g., Manual of Methods for General Bacteriology by the American Society for Bacteriology, Washington D.C., USA, 1981).

Carbon sources applicable in the medium may include sugars and carbohydrates such as glucose, saccharose, lactose, fructose, maltose, starch, and cellulose; oils and fats such as soybean oil, sunflower oil, castor oil, and coconut oil; fatty acids such as palmitic acid, stearic acid, and linoleic acid; alcohols such as ethanol and glycerol; and organic acids such as acetic acid. These substances may be used alone or in a mixture, but are not limited thereto.

Nitrogen sources applicable may include peptone, a yeast extract, a meat extract, a malt extract, corn steep liquor, soybean cake, and urea or inorganic compounds, such as ammonium sulfate, ammonium chloride, ammonium phosphate, ammonium carbonate, and ammonium nitrate. These nitrogen sources may also be used alone or in a mixture, but are not limited thereto.

Phosphorus sources applicable may include potassium dihydrogen phosphate or dipotassium hydrogen phosphate, or corresponding sodium-containing salts. In addition, the culture medium may include a metal salt such as magnesium sulfate or iron sulfate, which is required for the growth. Further, in addition to the above-described substances, essential growth factors such as amino acids and vitamins may be used, but are not limited thereto. Additionally, precursors suitable for the culture medium may be used. These substances may be appropriately added to the culture during culturing in a batch or continuous manner, but are not limited thereto.

Basic compounds such as sodium hydroxide, potassium hydroxide, or ammonia, or acidic compounds such as phosphoric acid or sulfuric acid may be added during culturing of the microorganism in a suitable manner, thereby adjusting the pH of the culture. In addition, an anti-foaming agent such as fatty acid polyglycol ester may be used to suppress the formation of bubbles. In order to maintain aerobic conditions, oxygen or oxygen-containing gas (e.g., air) may be injected into the culture, but is not limited thereto. The temperature of the culture may be usually 20° C. to 45° C., specifically 25° C. to 40° C. The culture may be continued until a desired amount of L-amino acid is produced, and it may generally be achieved within 10 hours to 160 hours, but is not limited thereto.

L-amino acids may be recovered from the culture by a common method known in the art. The recovering methods may include centrifugation, filtration, chromatography, crystallization, etc. For example, a supernatant, obtained by centrifuging the culture medium at a low speed and removing biomass, may be separated by ion exchange chromatography, but is not limited thereto.

The step of recovering may further include a purification process.

Still another aspect of the present disclosure provides a use of a microorganism of the genus *Corynebacterium* for enhancing productivity of L-amino acids, wherein the activity of a protein composed of the amino acid sequence of SEQ ID NO: 1 is inactivated.

Still another aspect of the present disclosure provides a method of enhancing productivity of L-amino acids, comprising: inactivating the activity of a protein composed of the amino acid sequence of SEQ ID NO: 1 in a microorganism of the genus *Corynebacterium*.

Advantageous Effects

The microorganism of the present disclosure producing L-amino acids may produce L-amino acids with a high yield. Further, the prepared L-amino acids may be applied to a variety of products, such as foods or food additives for humans or medical products as well as feeds or feed additives for animals.

MODE FOR INVENTION

Hereinafter, the present disclosure will be described in more detail with reference to Examples. However, these Examples are for illustrative purposes only, and the scope of the present disclosure is not intended to be limited by these Examples.

Example 1: Preparation of Random Mutant Library Using Transposon

To obtain a strain having improved lysine productivity, a vector library was prepared by the following method.

First, a plasmid obtained by using EZ-Tn5TM <R6Kγ/KAN-2>Tnp Transposome™ kit (Epicentre) was transformed into *Corynebacterium glutamicum* KCCM11016P (Korean Patent No. 10-0159812; this microorganism was disclosed as KFCC, and re-deposited to the Korean Culture Center of Microorganisms (KCCM), Yurim B/D, 45, Hongjenae-2ga-gil, Seodaemun-gu, Seoul 120-861, Republic of Korea under the Budapest Treaty with Accession No. KCCM11016P) as a parent strain by an electric pulse method (Appl. Microbiol. Biotechnol. 52:541-545, 1999), and smeared on a complex medium plate containing kanamycin (25 mg/L) to obtain about 20,000 colonies. During the pendency of this application, access to the invention will be afforded to the Commissioner upon request. All restrictions upon availability to the public will be irrevocably removed upon granting of the patent. The deposits will be maintained in a public depository for a period of 30 years or 5 years after the last request or for the effective life of the patent; whichever is longer. The deposits were viable at the time of deposit. The deposits will be replaced if they become non-viable.

<Complex Medium Plate (pH 7.0)>

10 g of glucose, 10 g of peptone, 5 g of beef extract, 5 g of yeast extract, 18.5 g of brain heart infusion, 2.5 g of NaCl, 2 g of urea, 91 g of sorbitol, 20 g of agar (based on 1 L of distilled water)

Example 2: Screening of Random Mutant Library Using Transposon

Each of about 20,000 colonies obtained in Example 1 was inoculated into 300 μL of the following selection medium, and cultured in a 96-deep well plate at 32° C. at 1000 rpm for about 24 hours.
<Selection Medium (pH 8.0)>
10 g of glucose, 5.5 g of ammonium sulfate, 1.2 g of $MgSO_4$ $7H_2O$, 0.8 g of $KH_2PO_4$, 16.4 g of $K_2HPO_4$, 100 μg of biotin, 1 mg of thiamine HCl, 2 mg of calcium pantothenate, 2 mg of nicotinamide (based on 1 L of distilled water)

A ninhydrin method was used to analyze the amount of produced L-lysine in the culture medium (Moore, S., Stein, W. H., Photometric ninhydrin method for use in the chromatography of amino acids. J. Biol. Chem. 1948, 176, 367-388).

Upon completion of the cultivation, 10 μL of the culture supernatant and 190 μL of a ninhydrin reaction solution were reacted at 65° C. for 30 minutes. Thereafter, absorbance was measured at a wavelength of 570 nm using a spectrophotometer, and about 60 kinds of colonies showing high absorbance were selected, as compared with a Corynebacterium glutamicum KCCM11016P strain, which is a control group. Other colonies were confirmed to show similar or decreased absorbance, as compared with that of the Corynebacterium glutamicum KCCM11016P strain used as the control group.

60 kinds of the selected strains were cultured in the same manner as above, and the ninhydrin reaction was repeatedly performed. As a result, the top 10 mutant strains having improved L-lysine productivity, compared to the Corynebacterium glutamicum KCCM11016P strain as the parent strain, were selected.

Example 3: Analysis of L-Lysine Productivity of Selected Mutant Strains

In order to finally select strains having increased L-lysine productivity, culturing was carried out by the following method for 10 kinds of the mutant strains selected in Example 2. Each of the strains was inoculated in a 250 mL corner-baffled flask containing 25 mL of the seed medium, and cultured under shaking at 30° C. and 200 rpm for 20 hours. Thereafter, 1 mL of the seed culture was inoculated in a 250 mL corner-baffled flask containing 24 mL of the production medium, and cultured under shaking at 32° C. and 200 rpm for 72 hours. Each of the seed medium and production medium has the following compositions. Upon completion of the cultivation, L-lysine concentrations in the culture medium were analyzed using HPLC (Waters, 2478), and the L-lysine concentration of each mutant strain is shown in Table 1 below.
<Seed Medium (pH 7.0)>
20 g of glucose, 10 g of peptone, 5 g of yeast extract, 1.5 g of urea, 4 g of $KH_2PO_4$, 8 g of $K_2HPO_4$, 0.5 g of $MgSO_4.7H_2O$, 100 μg of biotin, 1 mg of thiamine HCl, 2 mg of calcium pantothenate, 2 mg of nicotinamide (based on 1 L of distilled water)
<Production Medium (pH 7.0)>
100 g of glucose, 40 g of $(NH_4)_2SO_4$, 2.5 g of soy bean protein, 5 g of corn steep solid, 3 g of urea, 1 g of $KH_2PO_4$, 0.5 g of $MgSO_4.7H_2O$, 100 μg of biotin, 1 mg of thiamine HCl, 2 mg of calcium pantothenate, 3 mg of nicotinamide, 30 g of $CaCO_3$ (based on 1 L of distilled water)

TABLE 1

L-Lysine concentrations produced by 10 kinds of selected random mutant strains

| | | L-lysine (g/L) | | | |
|---|---|---|---|---|---|
| | Strain | Batch 1 | Batch 2 | Batch 3 | Average |
| Control group | KCCM11016P | 41.1 | 40.9 | 41.5 | 41.2 |
| 1 | KCCM11016P/mt-1 | 40.2 | 39.9 | 40.5 | 40.2 |
| 2 | KCCM11016P/mt-2 | 41.8 | 41.5 | 41.7 | 41.7 |
| 3 | KCCM11016P/mt-3 | 47.1 | 46.8 | 47 | 47.0 |
| 4 | KCCM11016P/mt-4 | 42.3 | 42.1 | 42.6 | 42.3 |
| 5 | KCCM11016P/mt-5 | 42.7 | 42.7 | 42.9 | 42.8 |
| 6 | KCCM11016P/mt-6 | 41.0 | 40.7 | 41.2 | 41.0 |
| 7 | KCCM11016P/mt-7 | 41.7 | 41.2 | 41.8 | 41.6 |
| 8 | KCCM11016P/mt-8 | 42.5 | 42.9 | 42.9 | 42.8 |
| 9 | KCCM11016P/mt-9 | 43.3 | 43.5 | 43.8 | 43.5 |
| 10 | KCCM11016P/mt-10 | 42.0 | 42.3 | 47.5 | 42.3 |

Among 10 kinds of the selected mutants above, KCCM11016P/mt-3 was finally selected as a strain having significantly improved L-lysine productivity.

Example 4: Identification of Cause of Increased L-Lysine Productivity in Finally Selected Strains In this Example, genes which are deleted due to random insertion of a transposon were identified in the mutant strains finally selected in Example 3.

Genomic DNA of KCCM11016P/mt-3 showing the most excellent L-lysine productivity was extracted and then digested. Thereafter, the resultant was ligated, transformed into E. coli DH5α, and then plated on an LB solid medium containing kanamycin (25 mg/L). After selecting 20 kinds of the transformed colonies, plasmids containing parts of the unknown genes were obtained, and nucleotide sequences were analyzed using primer 1 (SEQ ID NO: 3) and primer 2 (SEQ ED NO: 4) in the EZ-Tn5™<R6Kγori/KAN-2>Tnp Transposome™ Kit.

As a result, it was confirmed that a polynucleotide sequence of SEQ ID NO: 2 was deleted. It was confirmed that the polynucleotide sequence of SEQ ID NO: 2 encodes an amino acid sequence of SEQ ID NO: 1, and that the polynucleotide sequence of SEQ ID NO: 2 was a regulatory protein, the functions of which are not clearly revealed, based on the nucleotide sequence reported in Genbank of NIH, USA.

```
Primer 1
(SEQ ID NO: 3):
ACCTACAACAAAGCTCTCATCAACC

Primer 2
(SEQ ID NO: 4):
CTACCCTGTGGAACACCTACATCT
```

Accordingly, in order to examine whether inactivation of the activity of the protein would affect L-lysine productivity, the gene was selected as a deletion candidate gene.

Example 5: Construction of Recombinant Vector for Gene Deletion

In this Example, in order to confirm whether inactivation of the protein composed of the amino acid sequence of SEQ ID NO: 1 would affect L-lysine production, a recombinant plasmid for deletion of the gene selected in Example 4 on the chromosome of the L-lysine-producing microorganism of the genus *Corynebacterium* was constructed. To this end, Primers 3 to 6 as shown in the following Table 2 were synthesized.

TABLE 2

Primers 3 to 6 for preparation of fragment for gene deletion

| Primer | Nucleotide sequence |
| --- | --- |
| Primer 3 (SEQ ID NO: 5) | GAATTCGCGCCCCACTGGCCCTTC |
| Primer 4 (SEQ ID NO: 6) | ACCCCGGCGGCGCTGCTCTGGAATCAC |
| Primer 5 (SEQ ID NO: 7) | GAGCAGCGCCGCCGGGGTTTAATTAAT |
| Primer 6 (SEQ ID NO: 8) | GCAGGTCGACCTGGTTACCGGTCTGAATC |

In detail, to delete ORF (SEQ ID NO: 2) of NCgl0275 gene, primer 3 (SEQ ID NO: 5), primer 4 (SEQ ID NO: 6), primer 5 (SEQ ID NO: 7), and primer 6 (SEQ ID NO: 8) (Table 2) were synthesized to have EcoRI and SalI restriction sites at 5'- and 3'-ends, respectively and the genomic DNA of the wild-type *Corynebacterium glutamicum* ATCC 13032 was used as a template to perform PCR (Sambrook et al, Molecular Cloning, a Laboratory Manual, Cold Spring Harbor Laboratories, 1989).

As a result, DNA fragments of 500 bp corresponding to the upstream and downstream regions of the gene were amplified. In this regard, the PCR conditions are as follows: 30 cycles, each consisting of denaturation at 95° C. for 30 seconds; annealing at 50° C. for 30 seconds; and elongation at 72° C. for 1 minute, followed by elongation at 72° C. for 7 minutes. A pDZ, vector (Korean Patent No. 10-0924065), which is not replicable in *Corynebacterium glutamicum*, and the DNA fragments amplified by PCR were treated with EcoRI and SalI restriction enzymes for chromosomal insertion, ligated with each other using a DNA ligase, transformed into *E. coli* DH5α, and then plated on an LB solid medium containing kanamycin (25 mg/L).

After selecting colonies transformed with the plasmid in which the desired gene was inserted through PCR, the plasmid was obtained using a plasmid extraction method, and designated as pDZ-ΔNCgl0275.

Example 6: Preparation of NCgl0275-Deleted Strain from *Corynebacterium glutamicum* KCCM11016P and Evaluation of L-Lysine Productivity Thereof Based on KCCM11016P strain which is a representative L-lysine-producing strain of the genus *Corynebacterium*, the NCgl0275-deleted strain selected from the above was prepared and evaluation of L-lysine productivity thereof was attempted.

In detail, the recombinant plasmid pDZ-ΔNCgl0275 constructed in Example 5 was transformed into L-lysine-producing *Corynebacterium glutamicum* KCCM11016P by homologous recombination on chromosome (van der Rest et al., Appl Microbiol Biotechnol 52:541-545, 1999).

Thereafter, secondary recombination was performed on a solid medium plate containing 4% sucrose, Chromosomal deletion of the gene of SEQ ID NO: 2 in the *Corynebacterium glutamicum* transformant in which the secondary recombination was completed was confirmed by PCR using primer 3 and primer 6. The recombinant strain was designated as *Corynebacterium glutamicum* KCCM11016P-NCgl0275.

To analyze L-lysine productivity of the prepared *Corynebacterium glutamicum* KCCM11016P-NCgl0275 strain, the parent strain (i.e., *Corynebacterium glutamicum* KCCM11016P strain) was also cultured by the following method.

Each of *Corynebacterium glutamicum* KCCM11016P as the parent strain and *Corynebacterium glutamicum* KCCM11016P-NCgl0275 prepared in Example 6 was inoculated in a 250 mL corner-baffled flask containing 25 mL of the following seed medium, and cultured under shaking at 30° C. and 200 rpm for 20 hours. Thereafter, 1 mL of the seed culture was inoculated in a 250 mL corner-baffled flask containing 24 mL of a production medium, and cultured under shaking at 30° C. and 200 rpm for 72 hours. The compositions of the seed medium and the production medium are as follows, respectively.

<Seed Medium (pH 7.0)>
20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 µg of biotin, 1 mg of thiamine HCl, 2 mg of calcium pantothenate, 2 mg of nicotinamide (based on 1 L of distilled water)

<Production Medium (pH 7.0)>
100 g of glucose, 40 g of $(NH_4)_2SO_4$, 2.5 g of soy bean protein, 5 g of corn steep solid, 3 g of urea, 1 g of $KH_2PO_4$, 0.5 g of $MgSO_4 \cdot 7H_2O$, 100 µg of biotin, 1 mg of thiamine HCl, 2 mg of calcium pantothenate, 3 mg of nicotinamide, 30 g of $CaCO_3$ (based on 1 L of distilled water)

Upon completion of the cultivation, L-lysine production was measured using HPLC, and the L, lysine concentrations thus analyzed are shown in Table 3 below.

TABLE 3

Analysis of L-lysine productivity of KCCM11016P and KCCM11016P-NCgl0275

| | | L-lysine (g/L) | | | |
| --- | --- | --- | --- | --- | --- |
| | Strain | Batch 1 | Batch 2 | Batch 3 | Average |
| Control group | KCCM1106P | 40.3 | 40.0 | 40.4 | 40.2 |
| Experimental group | KCCM1106P-NCgl0275 | 46.8 | 47.3 | 47.1 | 47.1 |

As shown in the above results, when NCgl0275 was deleted in the L-lysine-producing *Corynebacterium glutamicum* KCCM11016P, the L-lysine productivity was increased to 17.2% on average, as compared with that of the parent strain.

Accordingly, it was confirmed that L-lysine productivity was improved by inactivating the protein composed of the amino acid sequence of SEQ ID NO: 1 in the microorganism of the genus *Corynebacterium*.

Further, the KCCM11016P-NCgl0275 strain was designated as CA01-7512 and deposited at Korean Culture Center of Microorganisms (KCCM), Yurim B/D, 45, Hongjenae-2ga-gil, Seodaemun-gu, Seoul 120-861, Republic of Korea, and an International Depositary Authority under the Budapest Treaty, with Accession No. KCCM12153P on Nov. 7, 2017. During the pendency of this application, access to the invention will be afforded to the Commissioner upon request. All restrictions upon availability to the public will be irrevocably removed upon granting of the patent. The deposits will be maintained in a public depository for a period of 30 years or 5 years after the last request or for the effective life of the patent; whichever is longer. The deposits were viable at the time of deposit. The deposits will be replaced if they become non-viable.

Example 7: Preparation of NCgl0275-Deleted Strain from *Corynebacterium glutamicum* KCCM11347P and Evaluation of L-Lysine Productivity Thereof In order to examine whether the above effects are also shown in other L-lysine-producing *Corynebacterium glutamicum* strains, an NCgl0275-deleted strain was prepared from an L-lysine-producing *Corynebacterium glutamicum* KCCM11347P (Korean Patent No. 10-0073610; this microorganism was disclosed as KFCC10750, and re-deposited to the Korean Culture Center of Microorganisms (KCCM), Yurim B/D, 45, Hongjenae-2ga-gil, Seodaemun-gu, Seoul 120-861, Republic of Korea under the Budapest Treaty with Accession No. KCCM11347P) in the same manner as in Example 6, and designated as KCCM11347P-NCgl0275. During the pendency of this application, access to the invention will be afforded to the Commissioner upon request. All restrictions upon availability to the public will be irrevocably removed upon granting of the patent. The deposits will be maintained in a public depository for a period of 30 years or 5 years after the last request or for the effective life of the patent; whichever is longer. The deposits were viable at the time of deposit. The deposits will be replaced if they become non-viable.

Thereafter, the strain was cultured in the same manner as in Example 6. Upon completion of the cultivation, L-lysine production was measured using HPLC, and the L-lysine concentrations thus analyzed are shown in Table 4 below.

TABLE 4

Analysis of L-lysine productivity of KCCM11347P and KCCM11347P-NCgl0275

| | | L-lysine (g/L) | | | |
|---|---|---|---|---|---|
| | Strain | Batch 1 | Batch 2 | Batch 3 | Average |
| Control group | KCCM11347P | 38.8 | 39.1 | 38.7 | 38.9 |
| Experimental group | KCCM11347P-NCgl0275 | 44.1 | 44.4 | 44.2 | 44.2 |

As shown in the above results, it was confirmed that when NCgl0275 gene was deleted in the L-lysine-producing *Corynebacterium glutamicum* KCCM11347P, the L-lysine productivity was increased to 13.6% on average.

Accordingly, as in the result of Example 6, it was confirmed that L-lysine productivity was improved by inactivating the protein composed of the amino acid sequence of SEQ ID NO: 1 in the microorganism of the genus *Corynebacterium*, as compared with the non-modified microorganism.

Example 8: Preparation of NCgl0275-Deleted Strain from *Corynebacterium glutamicum* KCCM10770P and Evaluation of L-Lysine Productivity Thereof In order to examine whether the above effects are also shown in other L-lysine-producing *Corynebacterium glutamicum* strains, an NCgl0275-deleted strain was prepared from an L-lysine-producing *Corynebacterium glutamicum* KCCM10770P (Korean Patent No. 10-0924065) in the same manner as in Example 6, and designated as KCCM10770P-NCgl0275.

Thereafter, the strain was cultured in the same manner as in Example 6. Upon completion of the cultivation, L-lysine production was measured using HPLC, and the L-lysine concentrations thus analyzed are shown in Table 5 below.

TABLE 5

Analysis of L-lysine productivity of KCCM10770P and KCCM10770P-NCgl0275

| | | L-lysine (g/L) | | | |
|---|---|---|---|---|---|
| | Strain | Batch 1 | Batch 2 | Batch 3 | Average |
| Control group | KCCM10770P | 45.1 | 44.9 | 45.5 | 45.2 |
| Experimental group | KCCM10770P-NCgl0275 | 51.5 | 52.0 | 51.9 | 51.8 |

As shown in the above results, it was confirmed that when NCgl0275 gene was deleted in the L-lysine-producing *Corynebacterium glutamicum* KCCM10770P, the L-lysine productivity was increased to 14.6% on average.

Accordingly, as in the result of Example 7, it was confirmed that L-lysine productivity may be improved by inactivating the protein composed of the amino acid sequence of SEQ ID NO: 1 in various L-lysine-producing microorganisms of the genus *Corynebacterium*, as compared with the parent strain.

Example 9: Preparation of NCgl0275-Deleted Strain from *Corynebacterium glutamicum* CJ3P and Evaluation of L-Lysine Productivity Thereof In order to examine whether the above effects are also shown in other L-lysine-producing *Corynebacterium glutamicum* strains, an NCgl0275-deleted strain was prepared from an L-lysine-producing *Corynebacterium glutamicum* CJ3P (Binder et al. Genome Biology 2012, 13:R40) in the same manner as in Example 6, and designated as CJ3P-NCgl0275.

Thereafter, the strain was cultured in the same manner as in Example 6. Upon completion of the cultivation, L-lysine production was measured using HPLC, and the L-lysine concentrations thus analyzed are shown in Table 6 below.

TABLE 6

Analysis of L-lysine productivity of CJ3P and CJ3P-Ncgl0275

| | | L-lysine (g/L) | | | |
|---|---|---|---|---|---|
| | Strain | Batch 1 | Batch 2 | Batch 3 | Average |
| Control group | CJ3P | 7.6 | 7.4 | 7.9 | 7.6 |
| Experimental group | CJ3P-NCgl0275 | 8.7 | 8.9 | 8.7 | 8.8 |

As shown in the above results, it was confirmed that when NCgl0275 gene was deleted in the L-lysine-producing *Corynebacterium glutamicum* CJ3P, the L-lysine productivity was increased to 15.8% on average.

Accordingly, as in the results of Examples 6 to 8, it was confirmed that L-lysine productivity may be improved by inactivating the protein composed of the amino acid sequence of SEQ ID NO: 1 in various L-lysine-producing microorganisms of the genus *Corynebacterium*.

Example 10: Preparation of NCgl0275-Deleted Strain from *Corynebacterium glutamicum* KCCM11201P and Evaluation of L-Valine Productivity Thereof It was examined whether valine productivity is also improved by deleting the NCgl0275 gene in *Corynebacterium glutamicum* having L-valine productivity other than L-lysine productivity.

The recombinant plasmid pDZ-ΔNCgl0275 constructed in Example 5 was transformed into L-valine-producing *Corynebacterium glutamicum* KCCM11201P (Korean Patent No. 10-1117022) by homologous recombination on chromosome (van der Rest et al., Appl Microbiol Biotechnol 52:541-545, 1999). Thereafter, secondary recombination was performed on a solid medium plate containing 4% sucrose. A strain in which the NCgl0275 gene was deleted on chromosome was prepared from the *Corynebacterium glutamicum* transformant in which the secondary recombination was completed, by PCR using primer 3 and primer 6. The recombinant strain was designated as *Corynebacterium glutamicum* KCCM11201P-NCgl0275.

To analyze L-valine productivity of the prepared strain, the strain was cultured by the following method, and components of the culture medium were analyzed. The strain was inoculated in a 250 mL corner-baffled flask containing 25 mL of a production medium, and cultured under shaking at 30° C. and 200 rpm for 72 hours. Thereafter, L-valine concentrations were measured using HPLC, and the L-valine concentrations thus analyzed are shown in Table 7 below.

<Production Medium (pH 7.0)>

100 g of glucose, 40 g of ammonium sulfate, 2.5 g of soy bean protein, 5 g of corn steep solid, 3 g of urea, 1 g of dibasic potassium phosphate, 0.5 g of magnesium sulfate heptahydrate, 100 μg of biotin, 1 mg of thiamine HCl, 2 mg of calcium pantothenate, 3 mg of nicotinamide, 30 g of calcium carbonate (based on 1 L of distilled water)

TABLE 7

L-valine productivity of KCCM11201P and KCCM11201P-NCgl0275

| | | L-valine (g/L) | | | |
|---|---|---|---|---|---|
| | Strain | Batch 1 | Batch 2 | Batch 3 | Average |
| Control group | KCCM11201P | 2.8 | 2.7 | 2.9 | 2.8 |
| Experimental group | KCCM11201P-NCgl0275 | 3.3 | 3.8 | 3.4 | 3.5 |

As shown in the above results, it was confirmed that when the L-valine productivity of KCCM11201P-NCgl0275 strain was increased to 25.0%, as compared with that of the control group. That is, it was confirmed that L-valine productivity may be improved by deleting the NCgl0275 gene in the microorganisms of the genus *Corynebacterium*.

It was also confirmed that productivities of various L-amino acids may be improved by inactivating the protein composed of the amino acid sequence of SEQ ID NO: 1 in the microorganisms of the genus *Corynebacterium*.

Example 11: Preparation of NCgl0275-Deleted Strain from *Corynebacterium glutamicum* CJ7V and Evaluation of L-Valine Productivity Thereof In order to examine whether the above effects are also shown in other L-valine-producing *Corynebacterium glutamicum* strains, one kind of a mutation [ilvN(A42V); Biotechnology and Bioprocess Engineering, June 2014, Volume 19, issue 3, pp 456-467] was introduced into a wild-type *Corynebacterium glutamicum* ATCC14067 to prepare a strain having improved L-valine productivity.

In detail, genomic DNA of the wild-type *Corynebacterium glutamicum* ATCC14067 strain was extracted using a G-spin Total DNA extraction mini kit (intron, Cat. No 17045) according to the protocol provided in the kit. The genomic DNA was used as a template to perform PCR. To construct a vector for introducing A42V mutation into ilvN gene, a primer set of primer 7 (SEQ ID NO: 9) and primer 8 (SEQ ID NO: 10) and a primer set of primer 9 (SEQ ID NO: 11) and primer 10 (SEQ ID NO: 12) were used to obtain DNA fragments (A, B). PCR conditions are as follows: denaturation at 94° C. for 5 minutes, 25 cycles, each consisting of denaturation at 94° C. for 30 seconds; annealing at 55° C. for 30 seconds; and elongation at 72° C. for 60 seconds, followed by elongation at 72° C. for 7 minutes.

As a result, A and B fragments, each having a polynucleotide of 537 bp, were obtained. These two fragments as a template and primer 7 (SEQ ID NO: 9) and primer 10 (SEQ ID NO: 12) were used to perform Overlapping PCR. A PCR product of 1044 bp was obtained (hereinafter, referred to as "mutation-introduced fragment").

The obtained mutation-introduced fragment was treated with XbaI restriction enzyme (New England Biolabs, Beverly, Mass.), and then ligated into a pDZ vector, which had been treated with the same restriction enzyme, using T4 ligase (New England Biolabs, Beverly, Mass.). The prepared gene was transformed into *E. coli* DH5α, and then selected on a LB medium containing kanamycin. DNA was obtained using a DNA-spin plasmid DNA purification kit (iNtRON). The vector for introducing A42V mutation into the ilvN gene was designated as pDZ-ilvN(A42V).

TABLE 8

Primers 7 to 10 for preparation of fragments for introducing A42V mutation into ilvN gene

| Primer | Nucleotide sequence |
|---|---|
| Primer 7 (SEQ ID NO: 9) | aatttctagaggcagaccctattctatgaagg |
| Primer 8 (SEQ ID NO: 10) | agtgtttcggtctttacagacacgagggac |
| Primer 9 (SEQ ID NO: 11) | gtccctcgtgtctgtaaagaccgaaacact |
| Primer 10 (SEQ ID NO: 12) | aatttctagacgtgggagtgtcactcgcttgg |

Thereafter, the prepared recombinant plasmid pDZ-ilvN (A42V) was transformed into the wild-type *Corynebacterium glutamicum* ATCC14067 by homologous recombination on chromosome (van der Rest et al., Appl Microbiol Biotechnol 52:541-545, 1999). Then, secondary recombination was performed on a solid medium plate containing 4% sucrose. The gene fragment was amplified from the *Corynebacterium glutamicum* transformant in which the secondary recombination was completed, by PCR using primer 7 and primer 10. The mutation-introduced strain was confirmed by sequencing analysis. The recombinant strain was designated as *Corynebacterium glutamicum* CJ7V.

Lastly, from the *Corynebacterium glutamicum* CJ7V having L-valine productivity, NCgl0275-deleted strain was prepared in the same manner as in Example 9, and designated as CJ7V-NCgl0275. To compare L-valine productivity of the prepared strain, the strain was cultured in the same manner as in Example 9, and then L-valine concentrations were analyzed, and the L-valine concentrations thus analyzed are shown in Table 9 below.

TABLE 9

L-valine productivity of CJ7V and CJ7V-NCgl0275

| | | L-valine (g/L) | | | |
|---|---|---|---|---|---|
| | Strain | Batch 1 | Batch 2 | Batch 3 | Average |
| Control group | CJ7V | 3.2 | 3.7 | 3.3 | 3.4 |
| Experimental group | C7V-NCgl0275 | 3.9 | 4.2 | 3.9 | 4.0 |

As shown in the above results, it was confirmed that when the L-valine productivity of CJ7V-NCgl0275 strain was increased to 17.6%, as compared with that of the control group. That is, it was confirmed that L-valine productivity may be improved by deleting the NCgl0275 gene in various microorganisms of the genus *Corynebacterium* having L-valine productivity.

As in Examples 6 to 10, it was confirmed that productivities of various L-amino acids may be improved by inactivating the protein composed of the amino acid sequence of SEQ ID NO: 1 in the microorganisms of the genus *Corynebacterium*.

Example 12: Preparation of NCgl0275-Deleted Strain from *Corynebacterium glutamicum* CJ8V and Evaluation of L-Valine Productivity Thereof In order to examine whether the above effects are also shown in other L-valine-producing *Corynebacterium glutamicum* strains, one kind of a mutation [ilvN(A42V)] was introduced into a wild-type *Corynebacterium glutamicum* ATCC13869 in the same manner as in Example 10 to prepare a mutant strain having improved L-valine productivity. This recombinant strain was designated as *Corynebacterium glutamicum* CJ8V.

From the *Corynebacterium glutamicum* CJ8V having L-valine productivity, NCgl0275-deleted strain was prepared in the same manner as in Example 9, and designated as CJ8V-NCgl0275.

To compare L-valine productivity of the prepared strain, the strain was cultured in the same manner as in Example 9, and then L-valine concentrations were analyzed, and the L-valine concentrations thus analyzed are shown in Table 10 below.

TABLE 10

L-valine productivity of CJ8V and CJ8V-NCgl0275

| | | L-valine (g/L) | | | |
|---|---|---|---|---|---|
| | Strain | Batch 1 | Batch 2 | Batch 3 | Average |
| Control group | CJ8V | 2.5 | 2.8 | 2.8 | 2.7 |
| Experimental group | CJ8V-NCgl0275 | 3.7 | 3.6 | 3.4 | 3.4 |

As shown in the above results, it was confirmed that when the L-valine productivity of the CJ8V-NCgl0275 strain was increased to 25.9%, as compared with that of the control group. That is, as in Examples 10 to 11, it was confirmed that L-valine productivity may be improved by deleting the NCgl0275 gene in various microorganisms of the genus *Corynebacterium* having L-valine productivity.

Accordingly, as in Examples 6 to 11, it was confirmed that productivities of various L-amino acids may be improved by inactivating the protein composed of the amino acid sequence of SEQ ID NO: 1 in the microorganisms of the genus *Corynebacterium*.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the present disclosure is defined by the appended claims rather than by the description preceding them, and therefore all changes and modifications that fall within metes and bounds of the claims, or equivalents of such metes and bounds are therefore intended to be embraced by the claims.

[Accession Number]
Depositary Institution: Korean Culture Center of Microorganisms (KCCM) (International Depositary Authority)
Accession Number: KCCM12153P
Date of Deposit: Nov. 7, 2017

What is claimed is:

1. A microorganism of the genus *Corynebacterium* that produces an L-amino acid, wherein a protein comprising the amino acid sequence of SEQ ID NO: 1 is not expressed,
wherein the microorganism is *Corynebacterium glutamicum*, and wherein the L-amino acid is L-lysine or L-valine, and the microorganism has increased productivity of the L-amino acid, as compared to a parental microorganism in which the protein is intrinsically expressed.

2. A method of producing an L-amino acid, the method comprising:

culturing the microorganism of claim 1 in a medium; and recovering the L-amino acid from the microorganism or the medium.

* * * * *

UNITED STATES PATENT AND TRADEMARK OFFICE
CERTIFICATE OF CORRECTION

PATENT NO. : 11,180,784 B2  
APPLICATION NO. : 16/344205  
DATED : November 23, 2021  
INVENTOR(S) : Son et al.

Page 1 of 2

It is certified that error appears in the above-identified patent and that said Letters Patent is hereby corrected as shown below:

On the Title Page

Item (54), Column 1, Line 2, after "CORYNEBACTERIUM" insert --FOR--.

In the Specification

In Column 1, Line 2, after "CORYNEBACTERIUM" insert --FOR--.

In Column 2, Line 13, delete "ED" and insert --ID--.

In Column 2, Line 47, delete "L, isoleucine, L, alanine," and insert --L-isoleucine, L-alanine,--.

In Column 8, Lines 46-47, delete "EZ-Tn5TM <R6Kγ/KAN-2>Tnp" and insert --EZ-Tn5™ <R6Kγori/KAN-2>Tnp--.

In Column 8, Line 50, delete "KFCC," and insert --KFCC10881,--.

In Column 10, Line 21, delete "47.5" and insert --42.5--.

In Column 10, Line 41, delete "ED" and insert --ID--.

In Column 11, Line 67, delete "sucrose," and insert --sucrose.--.

In Column 12, Line 37 (Approx.), delete "L, lysine" and insert --L-lysine--.

In Column 12, Line 60, delete "NCg10275" and insert --NCgl0275--.

In Column 12, Line 64, before "an International" delete "and".

In Column 13, Line 15, delete "NCg10275" and insert --NCgl0275--.

Signed and Sealed this  
Eighth Day of March, 2022

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 11,180,784 B2

In Column 13, Line 23, delete "NCg10275." and insert --NCgl0275.--.

In Column 16, Line 40, delete "DH5a," and insert --DH5α,--.

In Column 17, Line 23-24, delete "C7V-NCgl0275" and insert --CJ7V-NCgl0275--.

SEQUENCE LISTING

<160> NUMBER OF SEQ ID NOS: 12

<210> SEQ ID NO 1
<211> LENGTH: 116
<212> TYPE: PRT
<213> ORGANISM: Corynebacterium glutamicum

<400> SEQUENCE: 1

Met Thr Ser Val Ile Pro Glu Gln Arg Asn Asn Pro Phe Tyr Arg Asp
1               5                   10                  15

Ser Ala Thr Ile Ala Ser Ser Asp His Thr Glu Arg Gly Glu Trp Val
            20                  25                  30

```
Thr Gln Ala Lys Cys Arg Asn Gly Asp Pro Asp Ala Leu Phe Val Arg
        35                  40                  45

Gly Ala Ala Gln Arg Arg Ala Ala Ile Cys Arg His Cys Pro Val
 50                  55                  60

Ala Met Gln Cys Cys Ala Asp Ala Leu Asp Asn Lys Val Glu Phe Gly
 65                  70                  75                  80

Val Trp Gly Gly Leu Thr Glu Arg Gln Arg Arg Ala Leu Leu Arg Lys
                85                  90                  95

Lys Pro His Ile Thr Asn Trp Ala Glu Tyr Leu Ala Gln Gly Gly Glu
            100                 105                 110

Ile Ala Gly Val
        115

<210> SEQ ID NO 2
<211> LENGTH: 351
<212> TYPE: DNA
<213> ORGANISM: Corynebacterium glutamicum

<400> SEQUENCE: 2
atgacgtctg tgattccaga gcagcgcaac aaccccttt ataggacag cgccacaatt        60 gcttcctcgg accacacaga gcgtggtgag tgggtcactc aggcaaagtg tcgaaatggc       120
gacccagatg cattgtttgt tcgtggtgca gcgcaacgcc gagcagcagc aatttgccgc       180
cactgccctg tagccatgca gtgctgcgcc gatgccttag ataacaaggt ggaattcgga       240
gtctggggag gcctgaccga gcgccagcgc cgtgcattgc ttcgaaagaa gccgcacatt       300
actaactggg ctgaatattt ggctcagggg ggcgagatcg ccggggttta a               351

<210> SEQ ID NO 3
<211> LENGTH: 25
<212> TYPE: DNA
<213> ORGANISM: Artificial Sequence
<220> FEATURE:
<223> OTHER INFORMATION: primer 1

<400> SEQUENCE: 3
acctacaaca aagctctcat caacc                                            25

<210> SEQ ID NO 4
<211> LENGTH: 24
<212> TYPE: DNA
<213> ORGANISM: Artificial Sequence
<220> FEATURE:
<223> OTHER INFORMATION: primer 2

<400> SEQUENCE: 4
ctaccctgtg gaacacctac atct                                             24

<210> SEQ ID NO 5
<211> LENGTH: 24
<212> TYPE: DNA
<213> ORGANISM: Artificial Sequence
<220> FEATURE:
<223> OTHER INFORMATION: primer 3

<400> SEQUENCE: 5
gaattcgcgc cccactggcc cttc                                             24

<210> SEQ ID NO 6
<211> LENGTH: 27
<212> TYPE: DNA
```

<213> ORGANISM: Artificial Sequence
<220> FEATURE:
<223> OTHER INFORMATION: primer 4

<400> SEQUENCE: 6
accccggcgg cgctgctctg gaatcac                               27

<210> SEQ ID NO 7
<211> LENGTH: 27
<212> TYPE: DNA
<213> ORGANISM: Artificial Sequence
<220> FEATURE:
<223> OTHER INFORMATION: primer 5

<400> SEQUENCE: 7
gagcagcgcc gccggggttt aattaat                               27

<210> SEQ ID NO 8
<211> LENGTH: 29
<212> TYPE: DNA
<213> ORGANISM: Artificial Sequence
<220> FEATURE:
<223> OTHER INFORMATION: primer 6

<400> SEQUENCE: 8
gcaggtcgac ctggttaccg gtctgaatc                             29

<210> SEQ ID NO 9
<211> LENGTH: 32
<212> TYPE: DNA
<213> ORGANISM: Artificial Sequence
<220> FEATURE:
<223> OTHER INFORMATION: primer 7

<400> SEQUENCE: 9
aatttctaga ggcagaccct attctatgaa gg                         32

<210> SEQ ID NO 10
<211> LENGTH: 30
<212> TYPE: DNA
<213> ORGANISM: Artificial Sequence
<220> FEATURE:
<223> OTHER INFORMATION: primer 8

<400> SEQUENCE: 10
agtgtttcgg tctttacaga cacgagggac                            30

<210> SEQ ID NO 11
<211> LENGTH: 30
<212> TYPE: DNA
<213> ORGANISM: Artificial Sequence
<220> FEATURE:
<223> OTHER INFORMATION: primer 9

<400> SEQUENCE: 11
gtccctcgtg tctgtaaaga ccgaaacact                            30

<210> SEQ ID NO 12
<211> LENGTH: 32
<212> TYPE: DNA
<213> ORGANISM: Artificial Sequence
<220> FEATURE:
<223> OTHER INFORMATION: primer 10

```
<400> SEQUENCE: 12
aatttctaga cgtgggagtg tcactcgctt gg                                    32
```